(12) United States Patent
Birnkrant et al.

(10) Patent No.: US 11,067,457 B2
(45) Date of Patent: Jul. 20, 2021

(54) FIBER OPTIC BASED SMOKE AND/OR OVERHEAT DETECTION AND MONITORING FOR AIRCRAFT

(71) Applicant: Kidde Technologies, Inc., Wilson, NC (US)

(72) Inventors: Michael J. Birnkrant, Wethersfield, CT (US); Stefan Coreth, Roanoke Rapids, NC (US); Kenneth Bell, Epsom (GB); Jennifer M. Alexander, Roseville, MN (US); Peter R. Harris, West Hartford, CT (US); Antonio M. Vincitore, South Windsor, CT (US)

(73) Assignee: KIDDE TECHNOLOGIES, INC., Wilson, NC (US)

( * ) Notice: Subject to any disclaimer, the term of this patent is extended or adjusted under 35 U.S.C. 154(b) by 544 days.

(21) Appl. No.: 15/809,474

(22) Filed: Nov. 10, 2017

(65) Prior Publication Data

US 2018/0136053 A1    May 17, 2018

Related U.S. Application Data

(60) Provisional application No. 62/425,727, filed on Nov. 23, 2016, provisional application No. 62/420,675, filed on Nov. 11, 2016.

(51) Int. Cl.
*G01K 11/32* (2021.01)
*G01N 33/00* (2006.01)

(52) U.S. Cl.
CPC ......... *G01K 11/32* (2013.01); *G01N 33/0036* (2013.01)

(58) Field of Classification Search
CPC .... G01K 11/32; G01N 33/0036; G08B 17/06; G08B 17/107
See application file for complete search history.

(56) References Cited

U.S. PATENT DOCUMENTS

| 4,491,830 A | * | 1/1985 | Miyabe | ... G08B 17/00 340/518 |
| 4,701,624 A | | 10/1987 | Kern et al. | |

(Continued)

FOREIGN PATENT DOCUMENTS

| CN | 102280004 A | 12/2011 |
| CN | 104392576 A | 3/2015 |

(Continued)

OTHER PUBLICATIONS

European Search Report Issued in EP Application No. 17201040.7, dated Apr. 12, 2018, 13 Pages.

(Continued)

*Primary Examiner* — Lisa M Caputo
*Assistant Examiner* — Janice M Soto
(74) *Attorney, Agent, or Firm* — Cantor Colburn LLP

(57) ABSTRACT

A method of monitoring smoke, fire, and temperature conditions includes transmitting light through a first fiber optic cable, the fiber optic cable terminating at a node disposed to monitor a smoke or fire condition at one or more predetermined areas, transmitting light along a second fiber optic cable, the second fiber optic cable arranged to monitor a temperature condition at one or more predetermined areas, receiving scattered light from the first fiber optic cable and/or the second fiber optic cable at a control system, and analyzing the scattered light to determine at least one of the presence and magnitude of smoke, fire and/or a temperature condition along the fiber harness or at the node.

17 Claims, 21 Drawing Sheets

(56) References Cited

U.S. PATENT DOCUMENTS

| | | | |
|---|---|---|---|
| 5,051,590 A | | 9/1991 | Kern et al. |
| 5,051,595 A | | 9/1991 | Kern et al. |
| 6,960,019 B2 | | 11/2005 | Dammann |
| 8,075,181 B1 | * | 12/2011 | Stauffer ................. G01K 1/026 374/137 |
| 2001/0048071 A1 | * | 12/2001 | Holz .................. G01D 5/35383 250/227.12 |
| 2007/0280329 A1 | * | 12/2007 | Kawauchi ................. G01J 5/08 374/131 |
| 2013/0322490 A1 | * | 12/2013 | Bell ................... G01K 11/3206 374/161 |
| 2016/0258808 A1 | * | 9/2016 | Cedilnik ............... G01J 1/0425 |

FOREIGN PATENT DOCUMENTS

| | | |
|---|---|---|
| EP | 1887536 A1 | 2/2008 |
| JP | 0291548 A | 3/1990 |
| JP | 0418697 A | 1/1992 |

OTHER PUBLICATIONS

Chinese Office Action for Chinese Application No. 201711111401.4; dated May 28, 2020, 12 pages.

* cited by examiner

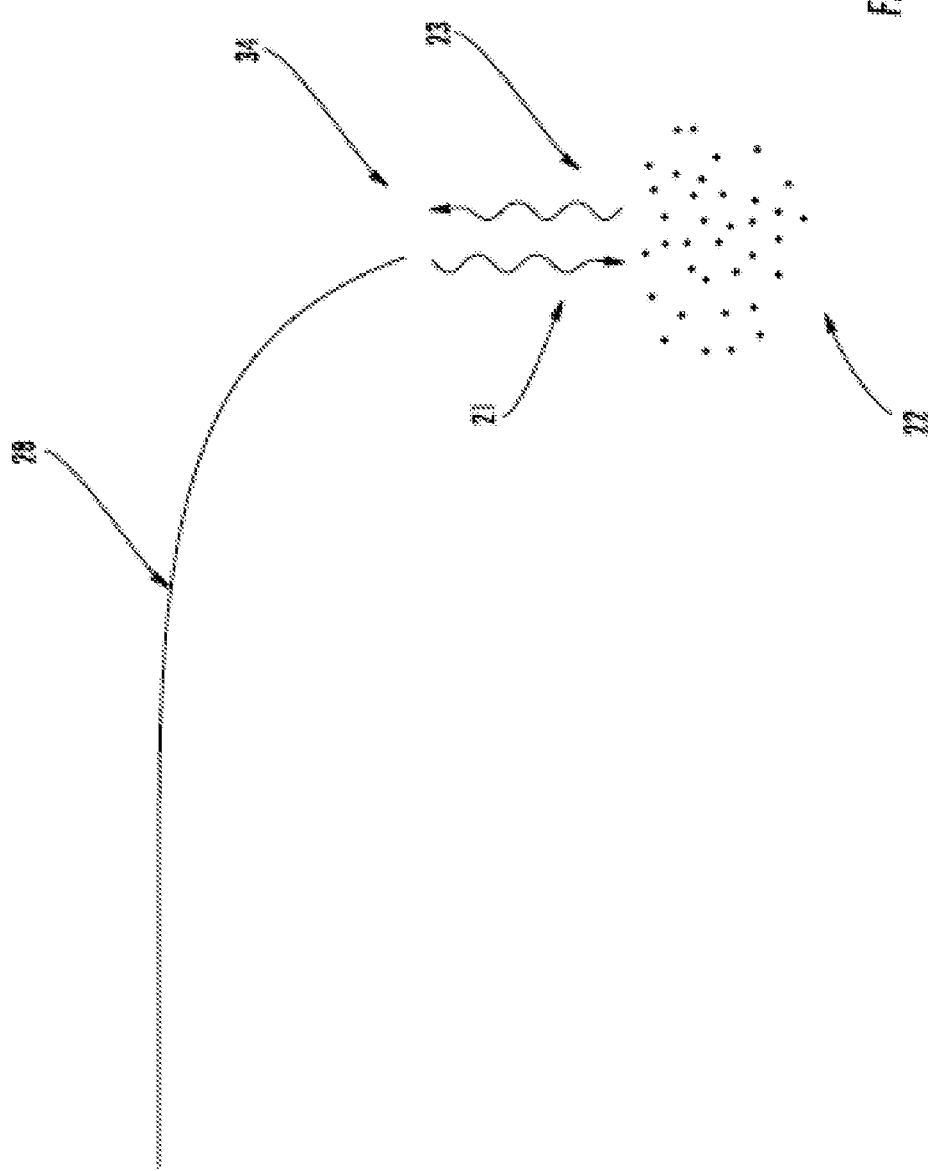

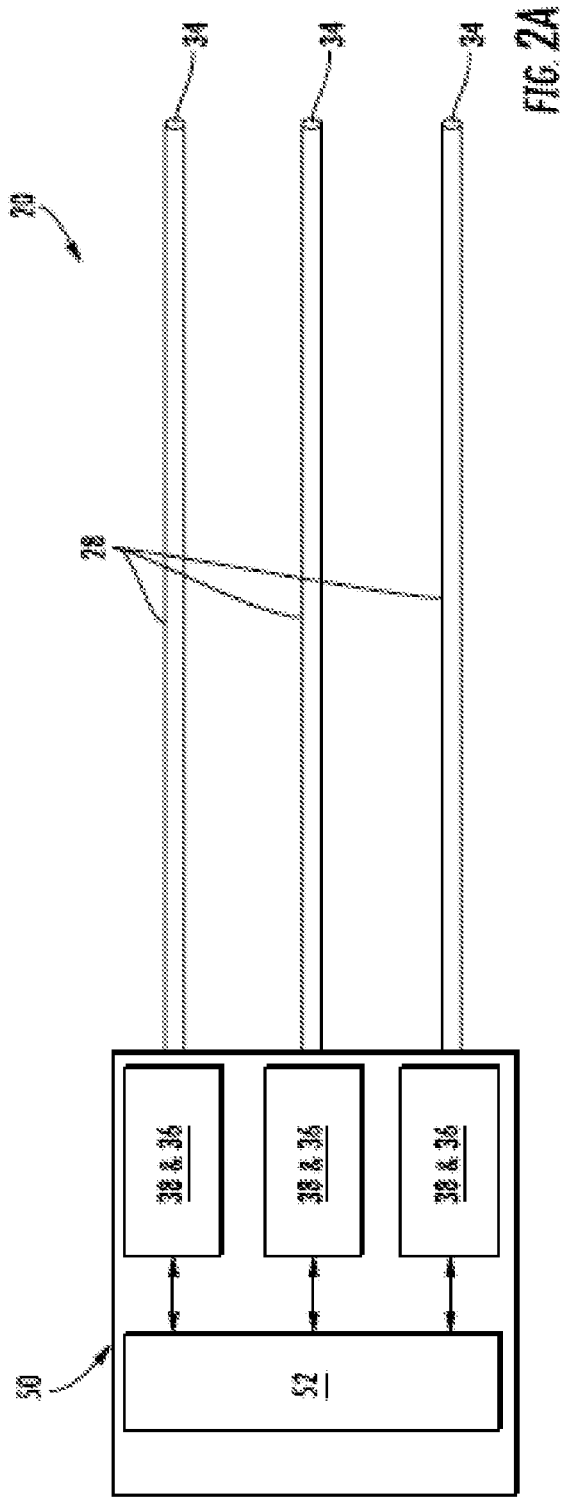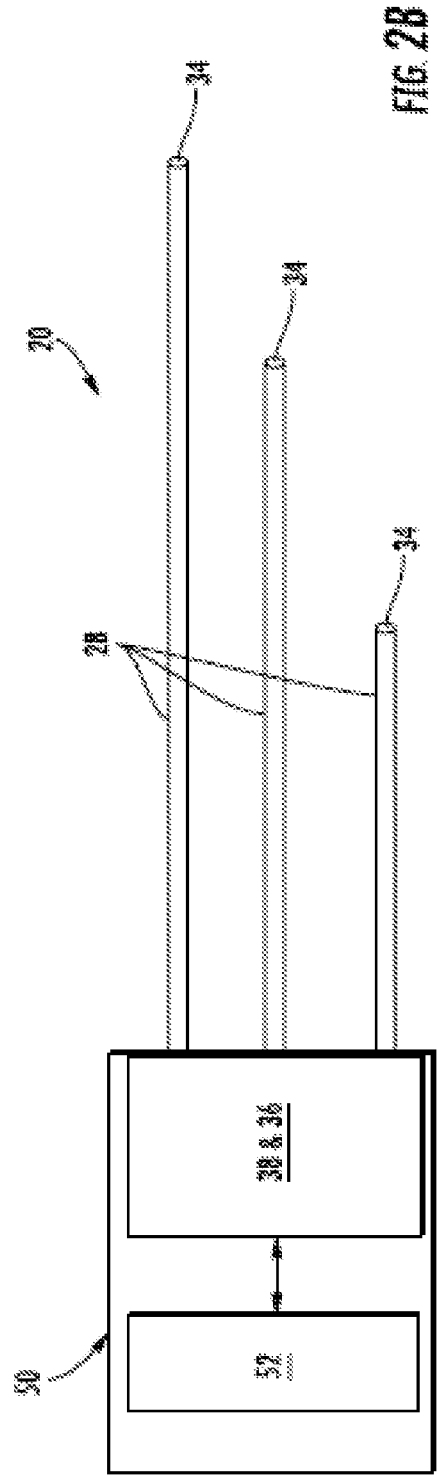

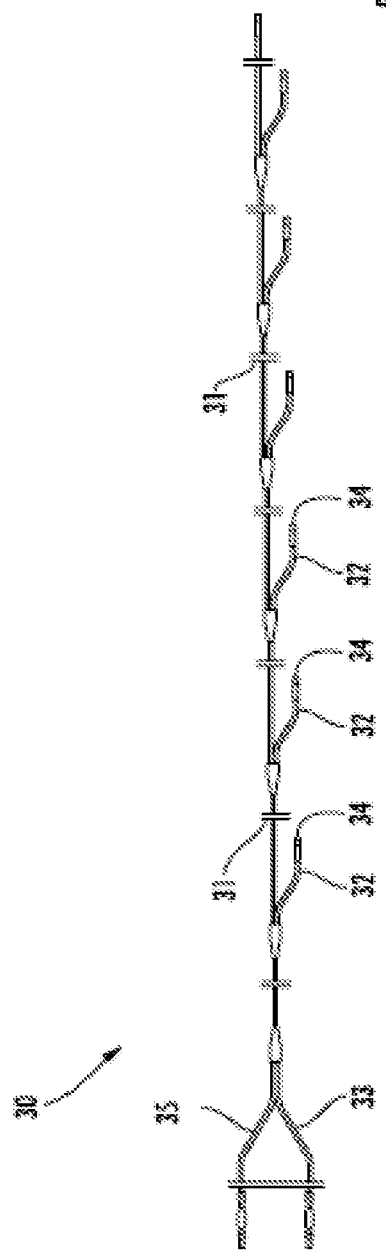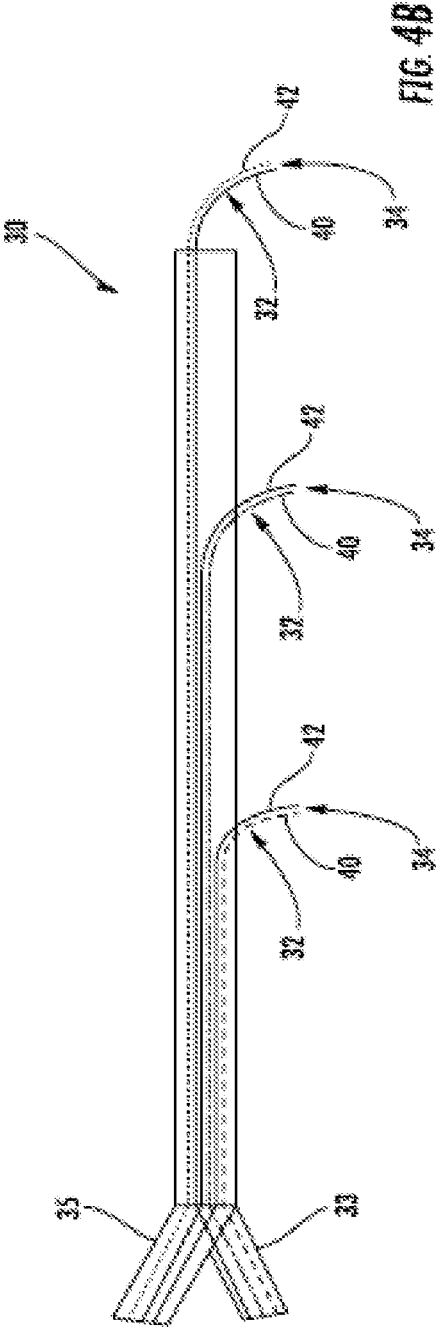

FIBER OPTIC BASED SMOKE AND/OR OVERHEAT DETECTION AND MONITORING FOR AIRCRAFT

CROSS-REFERENCE TO RELATED APPLICATIONS

This application claims the benefit of 62/425,727, filed Nov. 23, 2016, and this application claims the benefit of 62/420,675, filed Nov. 11, 2016 which are incorporated herein by reference in their entirety.

BACKGROUND

The present disclosure relates to aircraft operation, and more specifically to fire detection in an aircraft utilizing smoke and/or overheat detection.

Fire detection in aircraft utilizes smoke detection and overheat sensors to quickly and efficiently detect fires. Current aircraft regulations require that a system must detect a fire in the cargo compartment and provide visual indication to the crew within one minute. Further, lavatory systems and avionics bay systems conform to specific requirements for those areas. However, fires that are much smaller in size, in critical locations and sometimes in confined locations possess a special risk. Early reliable detection would allow for better control of the fire. Higher sensitivity enables earlier detection, but increases the risk of false alarms. Advances in signal processing and sensor design for point sensors and aspirating systems have decreased nuisance alarms by incorporating temperature and smoke detection.

However, overheat and smoke sensors are bulky, limiting their use to larger parts off the airplane, and can be prone to false alarms and are difficult to maintain. Further, such sensors typically require a weight and power budget, and can have difficulty detecting smoke in areas with a high airflow rate. Overheat detectors can have thermistor, eutectic salt, and pneumatic elements. The predominant approach utilizes eutectic salts, which is very sensitive and failsafe. However, the technology is prone to vibration, and is heavy and difficult to maintain during routine aircraft maintenance. New approaches that can reduce the footprint, are vibrationally insensitive and easily maintainable are advantageous. In addition, integrated fire protection technologies that reduce weight, power and foot print are advantageous to the air framer.

SUMMARY

In one embodiment, a method of monitoring smoke, fire, and temperature conditions includes transmitting light through a first fiber optic cable, the fiber optic cable terminating at a node disposed to monitor a smoke or fire condition at one or more predetermined areas, transmitting light along a second fiber optic cable, the second fiber optic cable arranged to monitor a temperature condition at one or more predetermined areas, receiving scattered light from the first fiber optic cable and/or the second fiber optic cable at a control system, and analyzing the scattered light to determine at least one of the presence and magnitude of smoke, fire and/or a temperature condition along the fiber harness or at the node.

Additionally or alternatively, in this or other embodiments the temperature condition is determined by analyzing the scattered light that has been internally scattered at one or more fiber portions of the second fiber optic cable.

Additionally or alternatively, in this or other embodiments the light source is selectively operable to transmit the light signal.

Additionally or alternatively, in this or other embodiments a wavelength of the transmitted light is selectably changed.

Additionally or alternatively, in this or other embodiments the light sensitive device is associated with the node, the light sensitive device configured to receive the scattered light signal.

Additionally or alternatively, in this or other embodiments the scattered light signal is converted into corresponding electrical signals for evaluation by a control unit.

In another embodiment, a system for monitoring smoke, fire and/or temperature conditions within an aircraft structure includes a fiber harness having a first fiber optic cable terminating at a node located to monitor a smoke or fire condition at one or more predetermined areas and a second fiber optic cable arranged to monitor a temperature condition at one or more predetermined areas. A control system is operably connected to the fiber harness. The control system includes one or more light sensitive devices configured to receive light from the first fiber optic cable and the second fiber optic cable, and a control unit configured to analyze light received at the one or more light sensitive devices from the first fiber optic cable to determine one or more fire or smoke conditions at one or more predetermined areas and analyze light received at the one or more light sensitive devices from the second fiber optic cable to determine the temperature conditions at one or more predetermined areas.

Additionally or alternatively, in this or other embodiments one or more fiber portions are located along the second fiber optic cable to measure an temperature via internal scattering of the light.

Additionally or alternatively, in this or other embodiments measuring the temperature further includes determining an overheat condition.

Additionally or alternatively, in this or other embodiments the one or more light sensitive devices includes a first light sensitive device configured to receive light from the first fiber optic cable and a second light sensitive device configured to receive light from the second fiber optic cable.

Additionally or alternatively, in this or other embodiments the control system includes a light source for transmitting the light signal along the first fiber optic cable and the second fiber optic cable.

Additionally or alternatively, in this or other embodiments the control unit is operably coupled to the light source to selectively control emission of light from the light source.

Additionally or alternatively, in this or other embodiments the light sensitive device is a photodiode.

Additionally or alternatively, in this or other embodiments the light sensitive device converts the scattered light signal received at the control system into an electrical signal receivable by the control unit.

Additionally or alternatively, in this or other embodiments the first fiber optic cable defines a plurality of nodes arranged within the aircraft structure.

Additionally or alternatively, in this or other embodiments the aircraft structure is one or more of a cargo compartment, an avionics bay or other enclosed portion of the aircraft.

In yet another embodiment, a method of monitoring a temperature condition includes transmitting light along a fiber optic cable, the fiber optic cable arranged to monitor a temperature condition at one or more predetermined areas, receiving scattered light from the fiber optic cable, communicating the scattered light to a light sensitive device, and determining, via the control system, whether the scattered light indicates a presence of an undesirable temperature condition along the fiber harness and/or at the node.

Additionally or alternatively, in this or other embodiments the light signal is internally scattered at one or more fiber portions of the second fiber optic cable, the internal scattering indicative of an undesirable temperature condition.

Additionally or alternatively, in this or other embodiments the light source is selectively operable to transmit the light signal.

Additionally or alternatively, in this or other embodiments a wavelength of the transmitted light is selectably changed.

BRIEF DESCRIPTION OF THE DRAWINGS

The subject matter, which is regarded as the present disclosure, is particularly pointed out and distinctly claimed in the claims at the conclusion of the specification. The foregoing and other features, and advantages of the present disclosure are apparent from the following detailed description taken in conjunction with the accompanying drawings in which:

FIG. 1B is a schematic diagram of light transmission at a node of a detection system according to an embodiment;

FIG. 2A is a schematic diagram of a detection system according to another embodiment;

FIG. 2B is a schematic diagram of a detection system according to another embodiment;

FIG. 4A is a side view of a fiber harness of a detection system according to an embodiment;

FIG. 4B is a schematic diagram of a fiber harness of a detection system according to an embodiment;

Figure 1A:
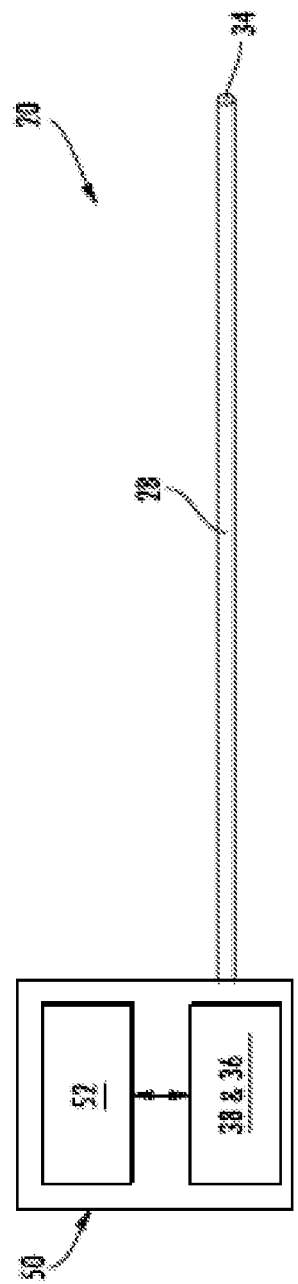
FIG. 1A is schematic diagram of a detection system according to an embodiment.

The detailed description explains embodiments of the present disclosure, together with advantages and features, by way of example with reference to the drawings.

DETAILED DESCRIPTION

Referring now to the FIGS., a system 20 for detecting one or more conditions or events within a designated area is illustrated. The detection system 20 may be able to detect one or more hazardous conditions, including but not limited to the presence of smoke, fire, temperature, flame, or any of a plurality of pollutants, combustion products, or chemicals. Alternatively, or in addition, the detection system 20 may be configured to perform monitoring operations of people, lighting conditions, or objects. In an embodiment, the system 20 may operate in a manner similar to a motion sensor, such as to detect the presence of a person, occupants, or unauthorized access to the designated area for example. The conditions and events described herein are intended as an example only, and other suitable conditions or events are within the scope of the disclosure.

The detection system 20 uses light to evaluate a volume for the presence of a condition. In this specification, the term "light" means coherent or incoherent radiation at any frequency or a combination of frequencies in the electromagnetic spectrum. In an example, the photoelectric system uses light scattering to determine the presence of particles in the ambient atmosphere to indicate the existence of a predetermined condition or event. In this specification, the term "scattered light" may include any change to the amplitude/intensity or direction of the incident light, including reflection, refraction, diffraction, absorption, and scattering in any/all directions. In this example, light is emitted into the designated area; when the light encounters an object (a person, smoke particle, or gas molecule for example), the light can be scattered and/or absorbed due to a difference in the refractive index of the object compared to the surrounding medium (air). Depending on the object, the light can be scattered in all different directions. Observing any changes in the incident light, by detecting light scattered by an object for example, can provide information about the designated area including determining the presence of a predetermined condition or event.

In its most basic form, as shown in FIG. 1, the detection system 20 includes a single fiber optic cable 28 with at least one fiber optic core. The term fiber optic cable 28 includes any form of optical fiber. As examples, an optical fiber is a length of cable that is composed of one or more optical fiber cores of single-mode, multimode, polarization maintaining, photonic crystal fiber or hollow core. A node 34 is located at the termination point of a fiber optic cable 32 and is inherently included in the definition of a fiber optic cable 28. The node 34 is positioned in communication with the ambient atmosphere. A light source 36, such as a laser diode for example, and a light sensitive device 38, such as a photodiode for example, are coupled to the fiber optic cable 28. A control system 50 of the detection system 20, discussed in further detail below, is utilized to manage the detection system operation and may include control of components, data acquisition, data processing and data analysis.

As shown in FIG. 1A, the light from the light source is transmitted through the node 34 to the surrounding area, illustrated schematically at 21. The light 21 interacts with one or more particles indicative of a condition, illustrated schematically at 22, and is reflected or transmitted back to the node 34, illustrated schematically at 23. A comparison of the light provided to the node 34 and/or changes to the light reflected back to the light sensitive device 38 from the node 34 will indicate whether or not changes in the atmosphere are present in the ambient atmosphere adjacent the node 34 that are causing the scattering of the light. The scattered light as described herein is intended to additionally include reflected, transmitted, and absorbed light. Although the detection system 20 is described as using light scattering to determine a condition or event, embodiments where light obscuration, absorption, and fluorescence is used in addition to or in place of light scattering are also within the scope of the disclosure.

In another embodiment, the detection system 20 can include a plurality of nodes 34. For example, as illustrated in FIG. 2A, a plurality of fiber optic cables 28 and corresponding nodes 34 are each associated with a distinct light sensitive device 38. In embodiments where an individual light sensitive device 38 is associated with each node 34, as shown in FIG. 2A, the signal output from each node 34 can be monitored. Upon detection of a predetermined event or condition, it will be possible to localize the position of the event because the position of each node 34 within the system 20 is known. Alternately, as shown in FIG. 2B, a plurality of fiber optic cables 28, may be coupled to a single light sensitive device.

In embodiments where a single light sensitive device 38 is configured to receive scattered light from a plurality of nodes 34, the control system 50 is able to localize the scattered light, i.e. identify the scattered light received from each of the plurality of nodes 34. In an embodiment, the control system 50 uses the position of each node 34, specifically the length of the fiber optic cables 28 associated with each node 34 and the corresponding time of flight (i.e. the time elapsed between when the light was emitted by the light source 36 and when the light was received by the light sensitive device 38), to associate different parts of the light signal with each of the respective nodes 34 that are connected to that light sensitive device 38. Alternatively, or in addition, the time of flight may include the time elapsed between when the light is emitted from the node and when the scattered light is received back at the node. In such embodiments, the time of flight provides information regarding the distance of the object relative to the node.

Figure 3:
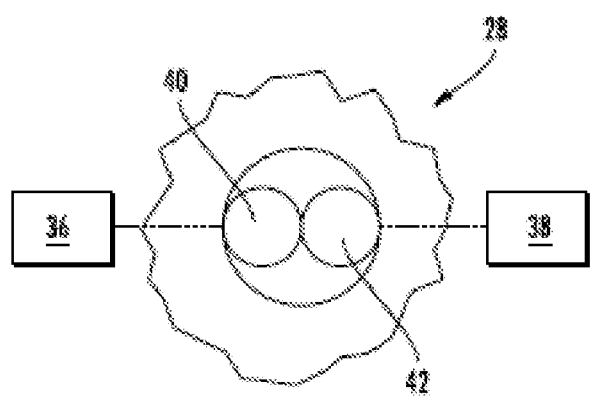
FIG. 3 is a cross-sectional view of a fiber optic node of the fiber harness of FIG. 1 according to an embodiment.

In an embodiment, illustrated in the cross-section of the fiber optic cable shown in FIG. 3, two substantially identical and parallel light transmission fiber cores 40, 42 are included in the fiber optic cable 28 and terminate at the node 34. However, it should be understood that embodiments where the fiber optic cable 28 includes only a single fiber core, or more than two cores are also contemplated herein. The light source 36 may be coupled to the first fiber core 40 and the light sensitive device 38 may be coupled to the second fiber core 42, for example near a first end of the fiber optic cable 28. The light source 36 is selectively operable to emit light, which travels down the first fiber core 40 of the fiber optic cable 28 to the node 34. At the node 34, the emitted light is expelled into the adjacent atmosphere. The light is scattered and transmitted back into the node 34 and down the fiber cable 28 to the light sensitive device 38 via the second fiber core 42.

With reference now to FIG. 4A, in more complex embodiments, the detection system 20 includes a fiber harness 30 having a plurality of fiber optic cables 28 bundled together. It should be noted that a fiber harness 30 can also be only a single fiber optic cable 28. In an embodiment, a plurality of fiber cores 40, 42 are bundled together at a location to form a fiber harness backbone 31 with the ends of the fiber optic cables 28 being separated (not included in the bundled backbone) to define a plurality of fiber optic branches 32 of the fiber harness 30. As shown, the plurality of fiber cores 40, 42 branch off to form a plurality of individual fiber branches 32, each of which terminates at a node 34. In the non-limiting embodiments of FIGS. 4A and 4B, the fiber harness 30 additionally includes an emitter leg 33 and a receiver leg 35 associated with the fiber branches 32. The emitter leg 33 may contain the first fiber cores 40 from each of the plurality of fiber branches 32 and the receiver leg 35 may contain all of the second fiber cores 42 from each of the fiber branches 32. The length of the fiber optic cores 40, 42 extending between the emitter leg 33 or the receiver leg 35 and the node 34 may vary in length such that the branches 32 and corresponding nodes 34 are arranged at various positions along the length of the fiber harness backbone 31. In an embodiment, the positions of the nodes 34 may be set during manufacture, or at the time of installation of the system 20.

Alternatively, the fiber harness 30 may include a fiber optic cable (not shown) having a plurality of branches 32 integrally formed therewith and extending therefrom. The branches 32 may include only a single fiber optic core. The configuration, specifically the spacing of the nodes 34 within a fiber harness 30 may be substantially equidistant, or may vary over the length of the harness 30. In an embodiment, the positioning of each node 34 may correlate to a specific location within the designated area.

Figure 5:
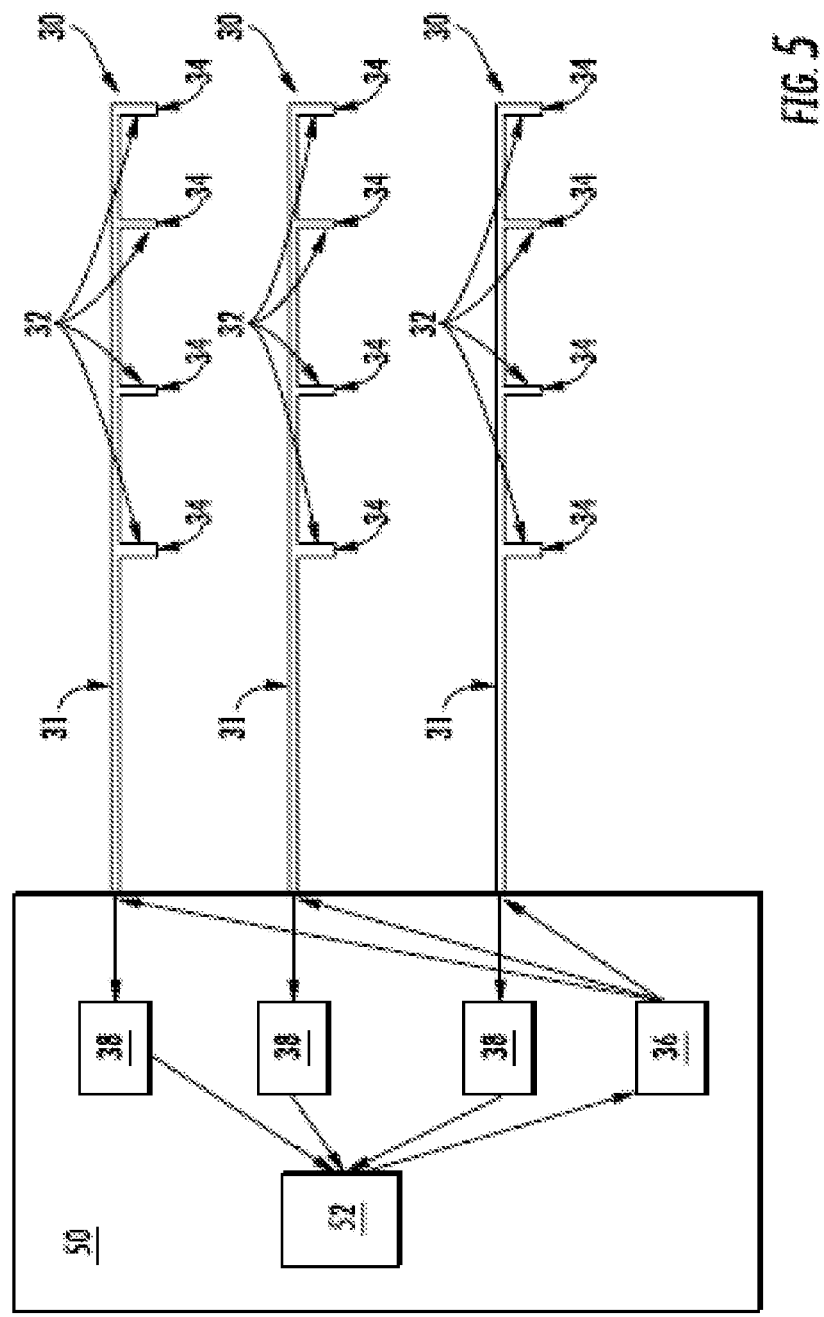
FIG. 5 is a schematic diagram of a detection system including a plurality of fiber harnesses according to an embodiment.

With reference now to FIG. 5, the detection system 20 may additionally include a plurality of fiber harnesses 30. In the illustrated, non-limiting embodiment, a distinct light sensitive device 38 is associated with each of the plurality of fiber harnesses 30. However, embodiments where a single light sensitive device 38 is coupled to the plurality of fiber harnesses 30 are also contemplated here. In addition, a single light source 36 may be operably coupled to the plurality of light transmission fiber cores 40 within the plurality of fiber harnesses 30 of the system 20. Alternatively, the detection system 20 may include a plurality of light sources 36, each of which is coupled to one or more of the plurality of fiber harnesses 30.

Figure 6:
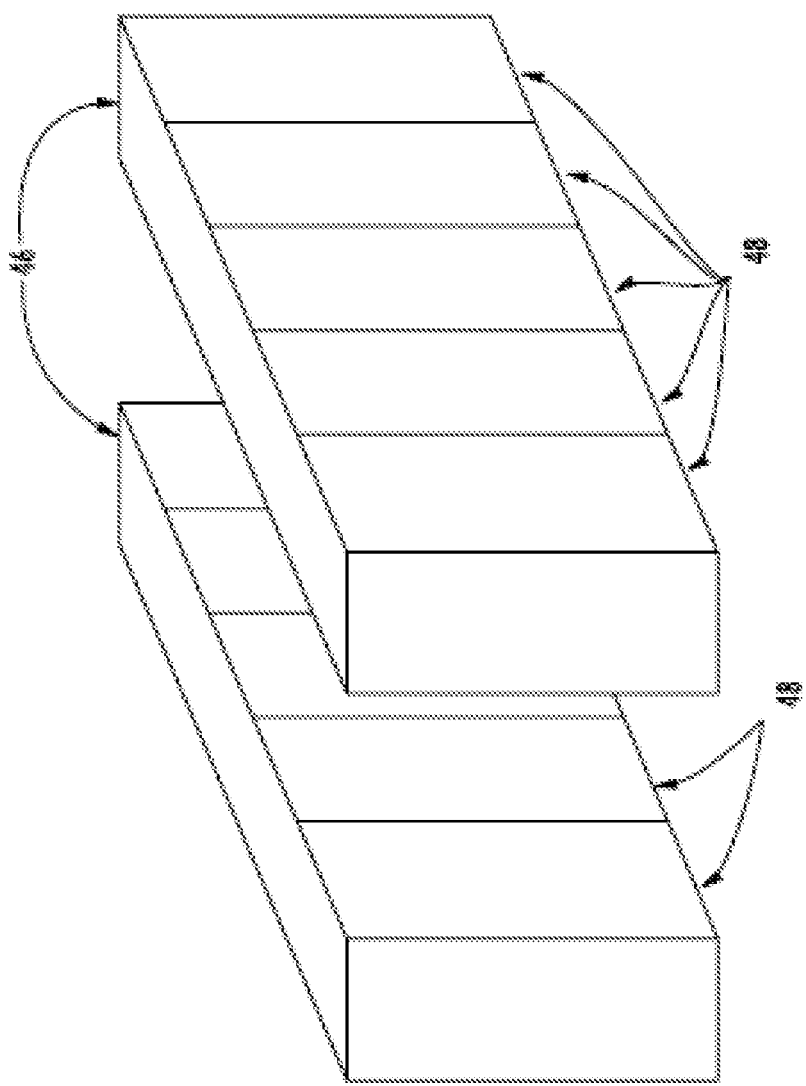
FIG. 6 is a perspective view of an area within a building to be monitored by a detection system according to an embodiment.

The detection system 20 may be configured to monitor a predetermined area such as a building. The detection system 20 may be especially utilized for predetermined areas having a crowded environment, such as a server room, as shown in FIG. 6 for example. Each fiber harness 30 may be aligned with one or more rows of equipment 46, and each node 34 therein may be located directly adjacent to one of the towers 48 within the rows 46. In addition, nodes may be arranged so as to monitor specific enclosures, electronic devices, or machinery. Positioning of the nodes 34 in such a manner allows for earlier detection of a condition as well as localization, which may limit the exposure of the other equipment in the room to the same condition. In another application, the detection system 20 may be integrated into an aircraft, such as for monitoring a cargo bay, avionics rack, lavatory, or another confined region of the aircraft that may be susceptible to fires or other events.

Figure 7:
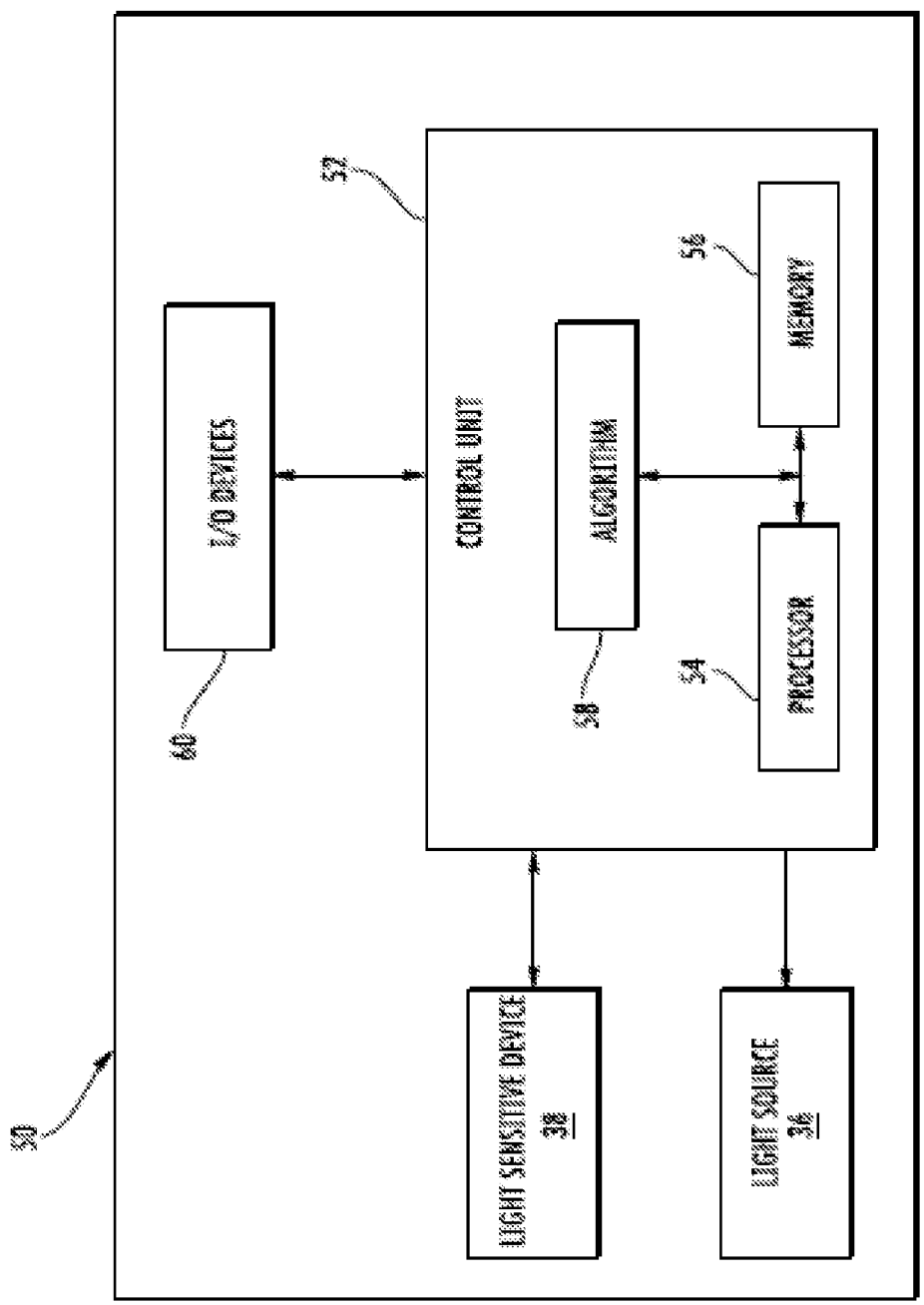
FIG. 7 is a schematic diagram of a control system of the detection system according to an embodiment.

The control system 50 of the detection system 20 is utilized to manage the detection system operation and may include control of components, data acquisition, data processing and data analysis. The control system 50, illustrated in FIG. 7, includes at least one light sensitive device 38, at least one light source, 36, and a control unit 52, such as a computer having one or more processors 54 and memory 56 for implementing an algorithm 58 as executable instructions that are executed by the processor 54. The instructions may be stored or organized in any manner at any level of abstraction. The processor 54 may be any type of processor, including a central processing unit ("CPU"), a general purpose processor, a digital signal processor, a microcontroller, an application specific integrated circuit ("ASIC"), a field programmable gate array ("FPGA"), or the like. Also, in some embodiments, memory 56 may include random access memory ("RAM"), read only memory ("ROM"), or other electronic, optical, magnetic, or any other computer readable medium for storing and supporting processing in the memory 56. In addition to being operably coupled to the at least one light source 36 and the at least one light sensitive device 38, the control unit 52 may be associated with one or more input/output devices 60. In an embodiment, the input/output devices 60 may include an alarm or other signal, or a fire suppression system which are activated upon detection of a predefined event or condition. It should be understood herein that the term alarm, as used herein, may indicate any of the possible outcomes of a detection.

The processor 54 may be coupled to the at least one light source 36 and the at least one light sensitive device 38 via connectors. The light sensitive device 38 is configured to convert the scattered light received from a node 34 into a corresponding signal receivable by the processor 54. In an embodiment, the signal generated by the light sensing device 38 is an electronic signal. The signal output from the light sensing device 38 is then provided to the control unit 52 for processing using an algorithm to determine whether a predefined condition is present.

The signal received by or outputted from the light sensitive device(s) 38 may be amplified and/or filtered, such as by a comparator (not shown), to reduce or eliminate irrelevant information within the signal prior to being communicated to the control unit 52 located remotely from the node 34. In such embodiments, the amplification and filtering of the signal may occur directly within the light sensing device 38, or alternatively, may occur via one or more components disposed between the light sensing device 38 and the control unit 52. The control unit 52 may control the data acquisition of the light sensitive device 38, such as by adjusting the gain of the amplifier, the bandwidth of filters, sampling rates, the amount of timing and data buffering for example.

Figure 8:
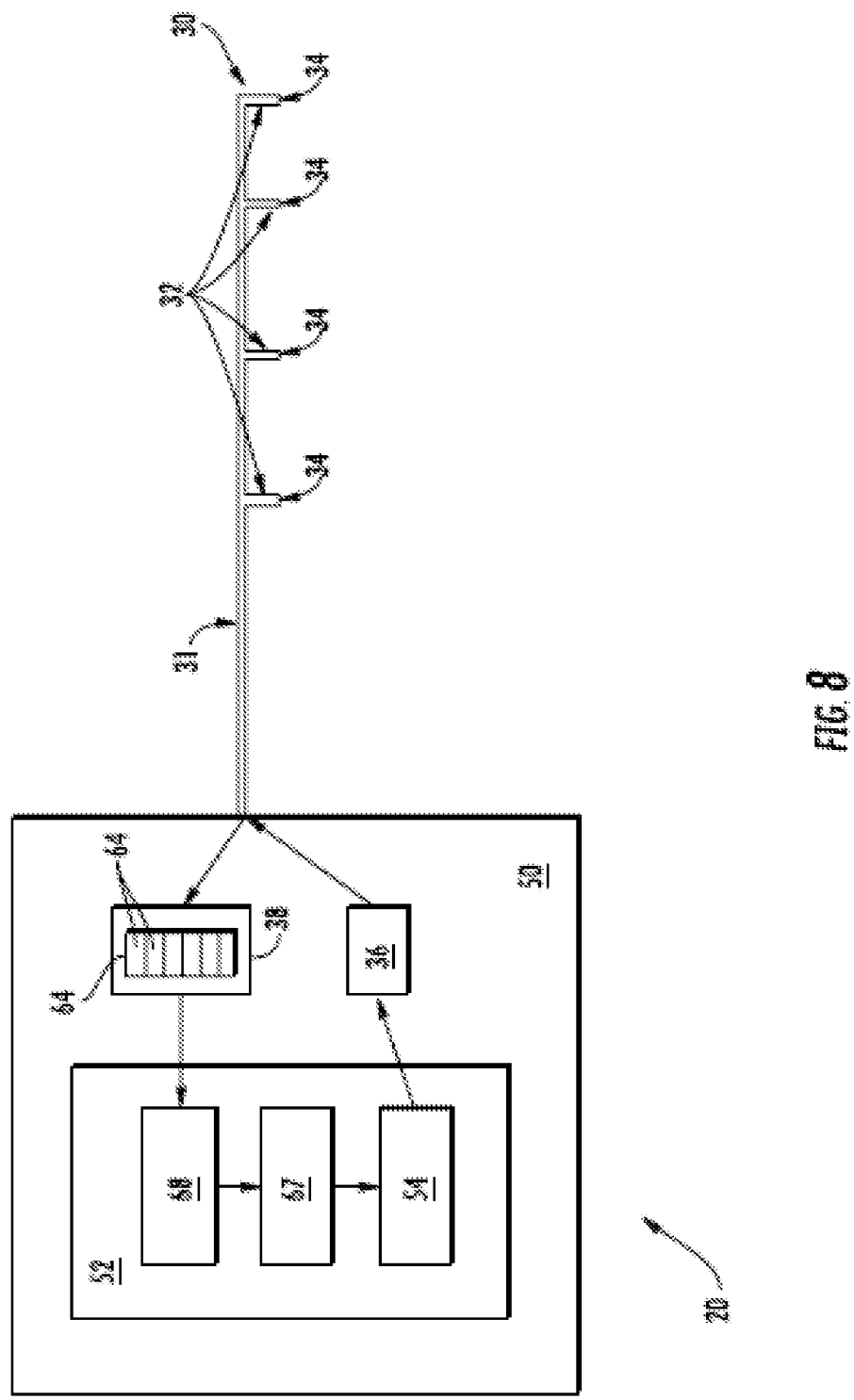
FIG. 8 is another schematic diagram of a detection system including an avalanche photo diode sensor according to an embodiment.

With reference now to FIG. 8, in an embodiment of the system 20, the light sensitive device 38 may include one or more Avalanche Photodiode (APD) sensors 64. For example, an array 66 of APD sensors 64 may be associated with the one or more fiber harnesses 30. In an embodiment, the number of APD sensors 64 within the sensor array 66 is equal to or greater than the total number of fiber harnesses 30 operably coupled thereto. However, embodiments where the total number of APD sensors 64 within the sensor array 66 is less than the total number of fiber harnesses 30 are also contemplated herein.

Data representative of the output from each APD sensor 64 in the APD array 66 is periodically taken by a switch 68, or alternatively, is collected simultaneously. The data acquisition 67 collects the electronic signals from the APD and associates the collected signals with metadata. The metadata as an example can be time, frequency, location or node. In an example, the electronic signals are from the APD are synchronized to the laser modulation such that the electrical signals are collected for a period of time that starts when the laser is pulsed to several microseconds after the laser pulse. The data will be collected and processed by the processor 54 to determine whether any of the nodes 34 indicates the existence of a predefined condition or event. In an embodiment, only a portion of the data outputted by the sensor array 66, for example the data from a first APD sensor 64 associated with a first fiber harness 30, is collected. The switch 68 is therefore configured to collect information from the various APD sensors 64 of the sensor array 66 sequentially. While the data collected from a first APD sensor 64 is being processed to determine if an event or condition has occurred, the data from a second APD 66 of the sensor array 66 is collected and provided to the processor 54 for analysis. When a predefined condition or event has been detected from the data collected from one of the APD sensors 64, the switch 68 may be configured to provide additional information from the same APD sensor 64 to the processor 54 to track the condition or event.

Figure 9:
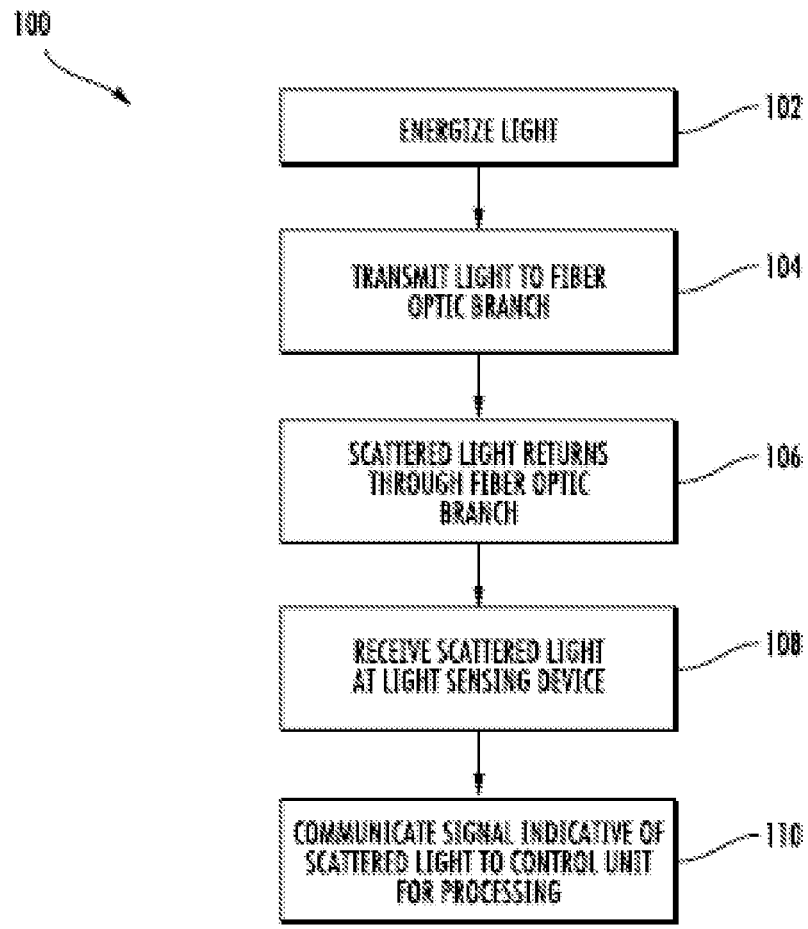
FIG. 9 is a method of operating a detection system according to an embodiment.

A method of operation 100 of the detection system 20 is illustrated in FIG. 9. The control unit 52 operably coupled to the light source 36 is configured to selectively energize the light source 36, as shown in block 102, and to emit light to a fiber harness 30 coupled thereto as shown in block 104. Based on the desired operation of the detection system 20, the control unit 52 may vary the intensity, duration, repetition, frequency, or other properties, of the light emitted. As the light travels down the first fiber core 40 of the at least one fiber optic branch 32, all or a portion of the light is emitted at one or more nodes 34 of the fiber harness 30. In block 106, light is scattered in the predetermined area and transmitted back through the fiber optic branches 32 via the second fiber cores 42. The scattered light may include one or more of scattered light within the atmosphere adjacent the node and scattered light that reflects from an interior of the fiber optic branch 32. The scattered light is transmitted to the at least one light sensing device 38 in block 108. As shown in block 110, the light sensing device 38 generates a signal in response to the scattered light received by each node 34, and provides that signal to the control unit 52 for further processing.

Figure 10:
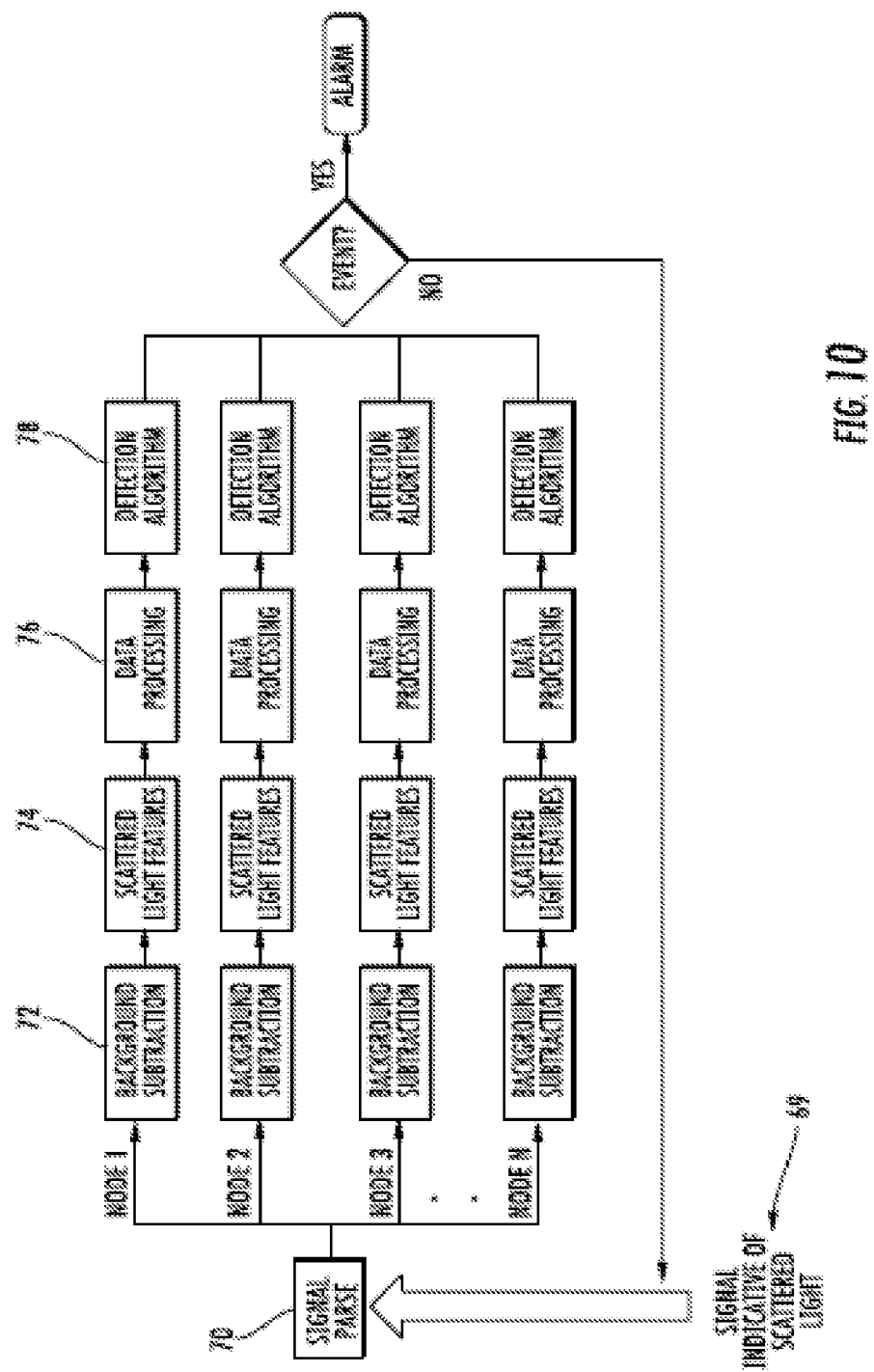
FIG. 10 is a schematic diagram of process flow for evaluating the signals generated by the light sensitive device according to an embodiment.

Using the algorithm 58 executed by the processor 54, each of the signals representing the scattered light received by the corresponding nodes 34 are evaluated to determine whether the light at the node 34 is indicative of a predefined condition, such as smoke for example. With reference to FIG. 10, a schematic diagram illustrating an example of a flow path for processing the signals generated by each of the nodes 34 is illustrated. As shown, the signal indicative of scattered light 69 is parsed, shown at block 70, into a plurality of signals based on their respective originating node 34. In the illustrated, non-limiting embodiment, background signals, illustrated schematically at 72, are subtracted from the data before the pulse features are evaluated for each of the individual signals. Through integration, pulse compression, and/or feature extraction, shown at block 74, one or more characteristics or features (pulse features) of the signal may be determined. Examples of such features include, but are not limited to, a peak height, an area under a curve defined by the signal, statistical characteristics such as mean, variance, and/or higher-order moments, correlations in time, frequency, space, and/or combinations thereof, and empirical features as determined by deep learning, dictionary learning, and/or adaptive learning and the like.

In an embodiment, the time of flight record is parsed and features are extracted. The time of flight record can cover a period of time. For example, a time of flight record can record light intensity over 0.001-1,000,000 nanoseconds, 0.1-100,000 nanoseconds, or 0.1-10,000 microseconds. The features extracted from the signal can include, but are not limited to height, full width at half maximum, signal pick up time, signal drop off time, group velocity, integration, rate of change, mean, and variance for example.

Through application of the data processing, illustrated schematically at block 76, the features may then be further processed by using, for example, smoothing, Fourier transforms or cross correlation. In an embodiment, the processed data is then sent to the detection algorithm at block 78 to determine whether or not the signal indicates the presence and/or magnitude of a condition or event at a corresponding node 34. This evaluation may be a simple binary comparison that does not identify the magnitude of deviation between the characteristic and a threshold. The evaluation may also be a comparison of a numerical function of the characteristic or characteristics to a threshold. The threshold may be determined a priori or may be determined from the signal. The determination of the threshold from the signal may be called background learning. Background learning may be accomplished by adaptive filtering, model-based parameter estimation, statistical modeling, and the like. In some embodiments, if one of the identified features does not exceed a threshold, the remainder of the detection algorithm is not applied in order to reduce the total amount processing done during the detection algorithm. In the event that the detection algorithm indicated the presence of the condition at one or more nodes 34, an alarm or other fire suppression system may, but need not be activated. It should be understood that the process for evaluating the data illustrated and described herein is intended as an example only and that other processes including some or all of the steps indicated in the FIG. are also contemplated herein.

The evaluation may also advantageously employ classifiers including those that may be learned from the signal via deep learning techniques including, but not limited to deep neural networks, convolutional neural networks, recursive neural networks, dictionary learning, bag of visual/depth word techniques, Support Vector Machine (SVM), Decision Trees, Decision Forests, Fuzzy Logic, and the like. The classifiers may also be constructed using Markov Model techniques, Hidden Markov Models (HMM), Markov Decision Processes (MDP), Partially Observable MDPs, Markov Decision Logic, Probabilistic Programming, and the like.

In addition to evaluating the signals generated from each node 34 individually, the processor 54 may additionally be configured to evaluate the plurality of signals or characteristics thereof collectively, such as through a data fusion operation to produce fused signals or fused characteristics. The data fusion operation may provide information related to time and spatial evolution of an event or predetermined condition. As a result, a data fusion operation may be useful in detecting a lower level event, insufficient to initiate an alarm at any of the nodes 34 individually. For example, in the event of a slow burning fire, the light signal generated by a small amount of smoke near each of the nodes 34 individually may not be sufficient to initiate an alarm. However, when the signals from the plurality of nodes 34 are reviewed in aggregate, the increase in light returned to the light sensitive device 38 from multiple nodes 34 may indicate the occurrence of an event or the presence of an object not otherwise detected. In an embodiment, the fusion is performed by Bayesian Estimation. Alternatively, linear or non-linear joint estimation techniques may be employed such as maximum likelihood (ML), maximum a priori (MAP), non-linear least squares (NNLS), clustering techniques, support vector machines, decision trees and forests, and the like.

As illustrated and described above, the processor 54 is configured to analyze the signals generated by at least one light sensing device 38 relative to time. In another embodiment, the detection algorithm may be configured to apply one or more of a Fourier transform, Wavelet transform, space-time transform, Choi-Williams distribution, Wigner-Ville distribution and the like, to the signals to convert the signals from a temporal domain to a frequency domain. This transformation may be applied to the signals when the nodes 34 are being analyzed individually, when the nodes 34 are being analyzed collectively during a data fusion, or both.

The relationship between the light scattering and the magnitude or presence of a condition is inferred by measuring a signal's causality and dependency. As an example, the measure of a causality utilizes one or more signal features as an input and determines one or more outputs from a calculation of a hypothesis testing method, foreground ratio, second derivative, mean or Granger Causality Test. Similarly, one or more signal features may be used as an input to evaluate the dependency of a signal. One or more outputs are selected from a calculation of a correlation, fast Fourier transform coefficients, a second derivative, or a window. The magnitude and presence of the condition is then based on the causality and dependency. The magnitude and presence of a condition may be calculated utilizing one or more evaluation approaches: a threshold, velocity, rate of change or a classifier. The detection algorithm may include utilizing the output from the calculation causality, dependency or both. This is used to indicate the presence of the condition at one or more nodes 34 and initiate a response.

Because the frequency of smoke varies within a small range, such as from about 0.01 Hz to about 10 Hz for example, evaluation of the signals with respect to frequency may effectively and accurately determine the presence of smoke within the predetermined space 82. The detection algorithm may be configured to evaluate the signals in a fixed time window to determine the magnitude of the frequency or the strength of the motion of the smoke. Accordingly, if the magnitude of a frequency component exceeds a predetermined threshold, the detection algorithm may initiate an alarm indicating the presence of a fire. In an embodiment, the predetermined threshold is about 10 Hz such that when the magnitude of the optical smoke frequency exceeds the threshold, smoke is present.

Figure 11B:
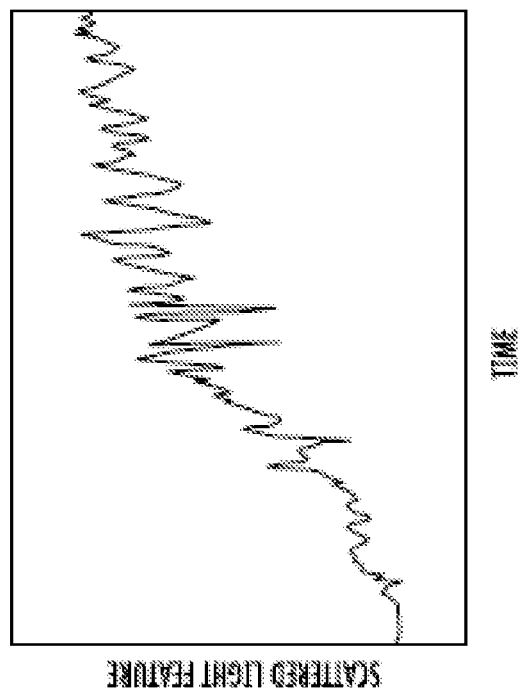
FIGS. 11A and 11B are diagrams illustrating the signals recorded by the detection system over time for various predefined conditions or events according to an embodiment.
Figure 11A:
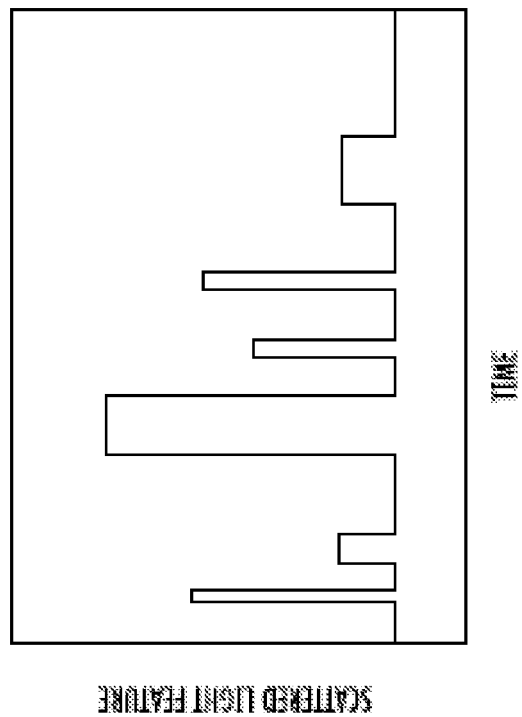

In an embodiment, the algorithm 58 is configured to distinguish between different events or conditions based on the rate of change in the light scattered by the atmosphere near the node 34 and received by one or more of the nodes 34 over time. With reference to FIGS. 11A and 11B, graphs of the signals recorded from a node 34 over time with respect to different events are illustrated. FIG. 11A indicates the change in the light signal received by a node 34 as a person walks through the area being monitored by the node 34. As shown in the graph, the movement of a person appears as steps having varying magnitudes. FIG. 11B, which represents the detection of smoke from a smoldering fire, appears graphically as a much continuously changing signal having an accelerating increase in the change in light signal received by a node 34 over time. It should be understood that the graphs illustrated are examples only. Further, each predefined event detectable by the detection system 20 may have one or more unique parameters associated therewith.

To reduce the noise associated with each signal, the light emitting device 36 may be modulated such that the device 36 is selectively operated to generate modulated light in a specific pattern. In an embodiment, the light within the pattern may vary in intensity, width, frequency, phase, and may comprise discrete pulses or may be continuous. The specific pattern of light may be designed to have desirable properties such as a specific autocorrelation with itself or cross-correlation with a second specific pattern. When the light is emitted in a specific pattern, the light scattered back to a corresponding light sensing device 38 should arrive in the substantially same pattern. Use of one or more specific and known patterns provides enhanced processing capabilities by allowing for the system 20 to reduce overall noise. This reduction in noise when combined with the signal processing may result in an improved signal to noise ratio and the total number of false events or conditions detected will decrease. Alternatively, or in addition, the device sensitivity may be improved thereby increasing the limits of the detection system 20. Similarly, by cross-correlating one or more second patterns, specific causes of transmitted or reflected signals may be distinguished, e.g. by Bayesian estimation of the respective cross-correlations of the received signal with the one or more second patterns.

In addition, modulation of the light signal emitted by the light source 36 may provide improved detection by determining more information about the event or condition causing the scatter in the light signal received by the node 34. For example, such modulation may allow the system 20 to more easily distinguish between a person walking through the designated area adjacent a node, as shown in FIG. 11A, and a smoldering fire adjacent the node 34.

Figure 12:
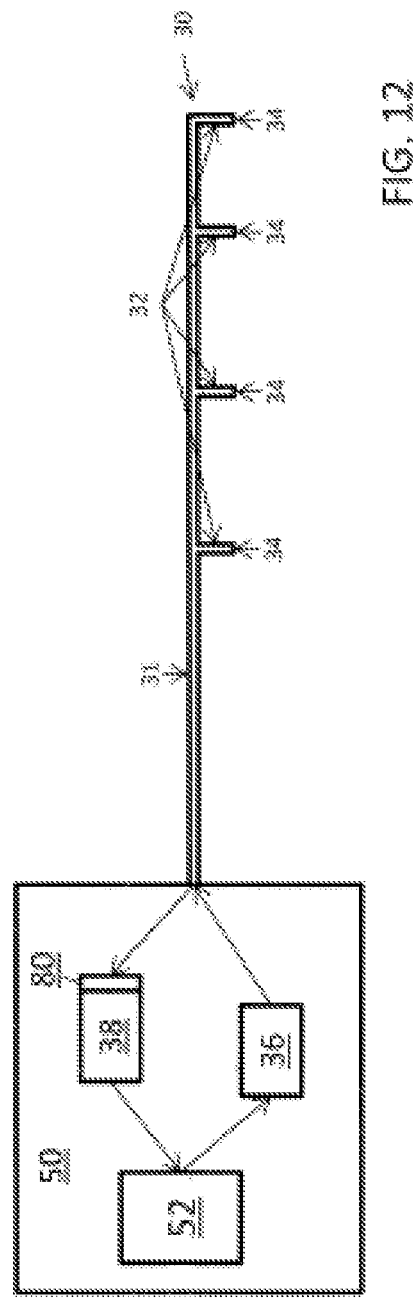
FIG. 12 is another schematic diagram of a detection system.

Referring now to FIG. 12, in some embodiments the system 20 includes one or more optical enhancement devices 80, such as a bandpass filter, a polarizer, an antireflective coating, a wave plate, and/or other optical features to reduce interference from non-event signals, or other non-desired signals, such as ambient light from either sunlight or lighting in the space, or from solid objects in the predetermined space 82. Further, the optical enhancement devices 80 may be utilized to reduce undesired wavelengths and/or intensities transmitted from the light source 36. The optical enhancement 80 is placed in the system 20 downstream of the light source 36, in some embodiments a laser diode, and upstream of the light sensitive device 38, in some embodiments the photodiode. The optical enhancement device 80 is placed so that light scattered and reflected back to the light sensitive device 38 is passed through the optical enhancement device 80 to filter or differentiate events or other conditions to be sensed from other signals due to, for example, ambient light, solid objects, bugs, dust, or water vapor.

As shown in FIG. 12, in some embodiments the optical enhancement 80 is located at the light sensitive device 38 and/or is a component of, integral to or embedded within the light sensitive device 38. Further, the light sensitive device 38 may be configured such that the optical enhancement device 80 is readily removable and/or replaceable with another optical enhancement 80 to filter or disseminate different conditions in the scattered/reflected signal.

Figure 13:
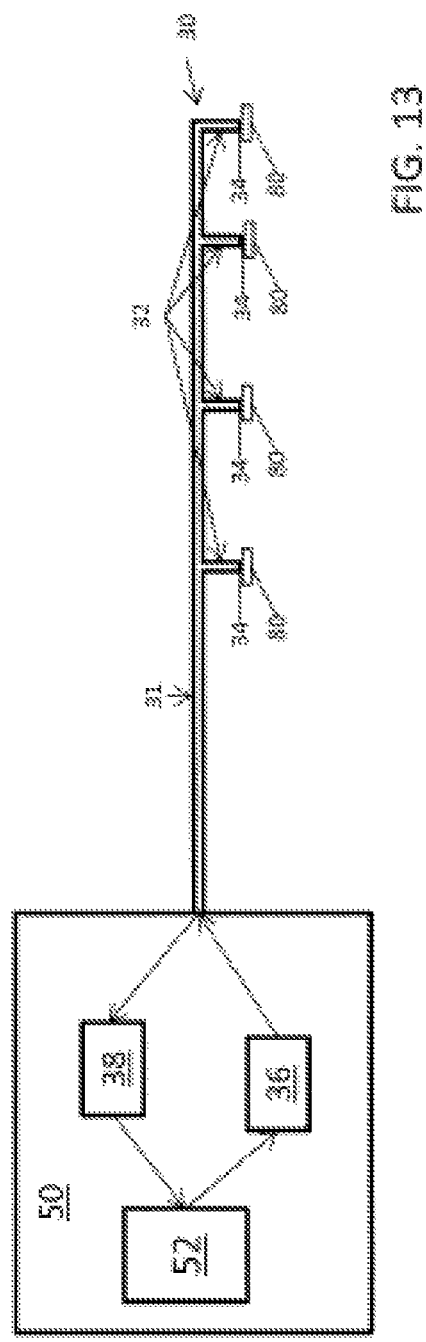
FIG. 13 is yet another schematic diagram of a detection system.

While in the embodiment of FIG. 12, the optical enhancement device 80 is located at the light sensitive device 38 or embedded in the light sensitive device 38, in other embodiments the optical enhancement device 80 is located at other locations, such as at the node 34 as shown in FIG. 13. This allows for node-specific placement of optical enhancement devices 80 such that different optical enhancement devices 80 may be placed at different nodes 34. Further, in some embodiments, combinations of optical enhancement devices 80, such as combinations of bandpass filters and polarizers, may be utilized to filter or disseminate certain conditions of the scattered/reflected light. Further, in systems 20 where the nodes 34 include two or more cores 40, 42, optical enhancements 80 may be located at an individual core 40, 42 or at two or more of the cores 40, 42.

Figure 14:
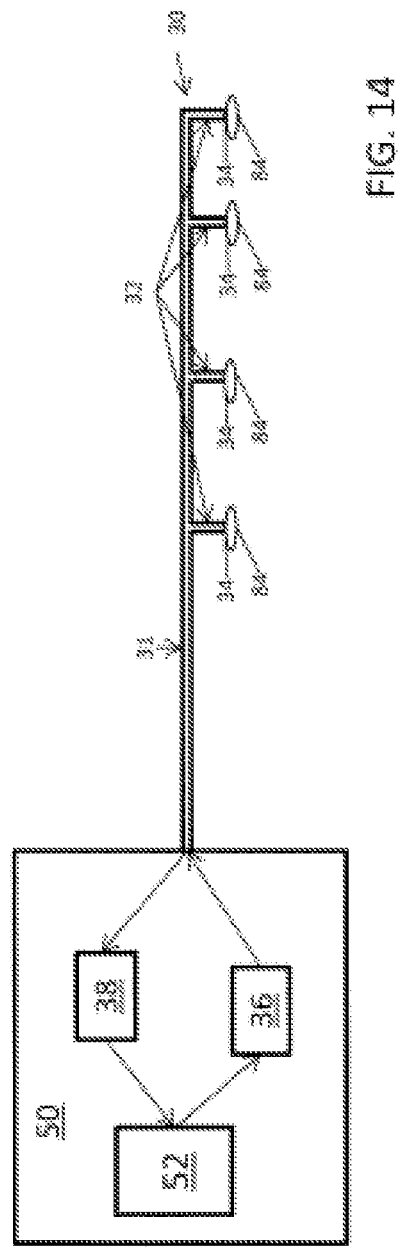
FIG. 14 is a schematic diagram of a detection system using lenses.

Referring now to FIG. 14, in some embodiments the system 20 includes focusing or expanding optical elements to increase range, sensitivity or field of view of the detection system 20 in detecting smoke/gas or other conditions or events. A focusing optical element can be placed at the node or between the control system and fiber harness to increase range and sensitivity by converging or collimating light. Also, an expanding optical element can be placed in similar locations to increase the field of view of the node by diverging the light. By way of example, optical elements may include mirrors, focusing lenses, diverging lenses, and diffusers, along with the integration of antireflective coatings on the optical elements or components thereof.

As shown in FIG. 14, the optical elements may be one or more lenses 84 located at the node 34. The lens 84 reduces divergence of the outgoing beam transmitted from the light source 36, while also increasing the amount of scattered light accepted by the node 34 for transmission to the light sensitive device 38. In some embodiments, the lens 84 is fused to the end of cores 40, 42 at the node 34 to reduce scattering of the light off of the lens 84 face, thereby enhancing light collection efficiency of the node 34. Further, in some embodiments, cores 40, 42 may have lensed and tapered fibers, which do not require fusing and function as a lens 84. In other embodiments, the lens 84 may be configured to reduce the scattering of light off of the lens face. Further, the lens 84 may include beam steering features, such as a solid state material which is utilized to change the refractive index of incident light to steer the light along the cores 40, 42. The beam steering feature may also be a photonic integrated circuit, which utilizes patterned silicon to control the directional emission of light.

Figure 15:
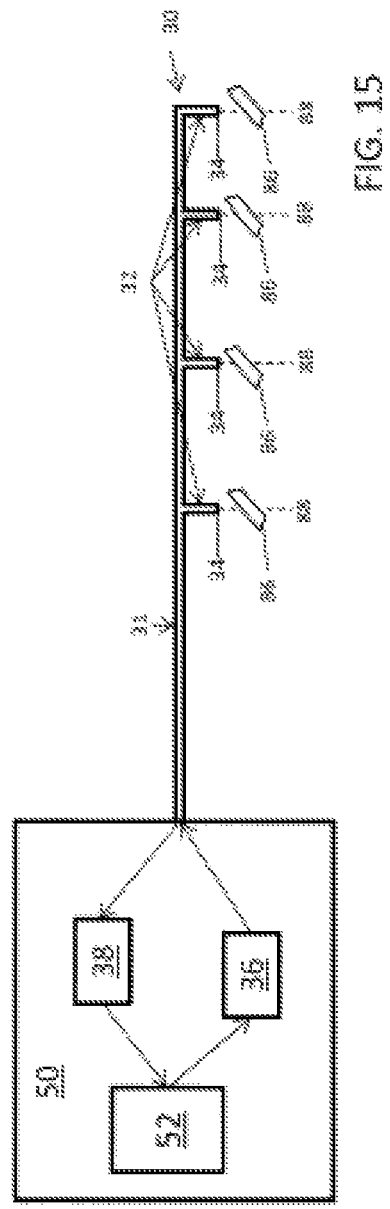
FIG. 15 is a another schematic diagram of a detection system using mirrors.

Referring now to FIG. 15, in some embodiments the optical elements may include a parabolic mirror 86 located at the node 34. The parabolic mirror 86 is located off-angle relative to a node axis 88. As with the lens 84, the parabolic mirror 86 reduces divergence of the outgoing beam transmitted from the light source 36, while also increasing an amount of scattered light accepted by the node 34 for transmission to the light sensitive device 38. In some embodiments, the parabolic mirror 86 is configured to rotate about a rotational axis during operation of the system 20 to further increase a coverage area of the node 34.

In some embodiments, both lens 84 and mirror 86 may be utilized at node 34. Further, while in the embodiments illustrated in FIGS. 14 and 15 optics are utilized at each node 34, in other embodiments, optics may be utilized only at selected nodes 34 to provide their benefits to the selected nodes 34, such as increasing detection range at selected nodes 34 due to, for example, constraints in placement of nodes 34 in the protected space. In other embodiments, the optical elements can be placed at the light source 36 or light sensitive device to enhance the detection system 50.

In addition to smoke or dust, the system 20 may be utilized to monitor or detect pollutants such as volatile organic compounds (VOC's), particle pollutants such as PM2.5 or PM10.0 particles, biological particles, and/or chemicals or gases such as $H_2$, $H_2S$, $CO_2$, $CO$, $NO_2$, $NO_3$, or the like. Multiple wavelengths may be transmitted by the light source 36 to enable simultaneous detection of smoke, as well as individual pollutant materials. For example, a first wavelength may be utilized for detection of smoke, while a second wavelength may be utilized for detection of VOC's. Additional wavelengths may be utilized for detection of additional pollutants, and using multiple wavelength information in aggregate may enhance sensitivity and provide discrimination of gas species from false or nuisance sources. In order to support multiple wavelengths, one or more lasers may be utilized to emit several wavelengths. Alternatively, the control system can provide selectively controlled emission of the light. Utilization of the system 20 for pollutant detection can lead to improved air quality in the predetermined space 82 as well as improved safety.

Figure 16:
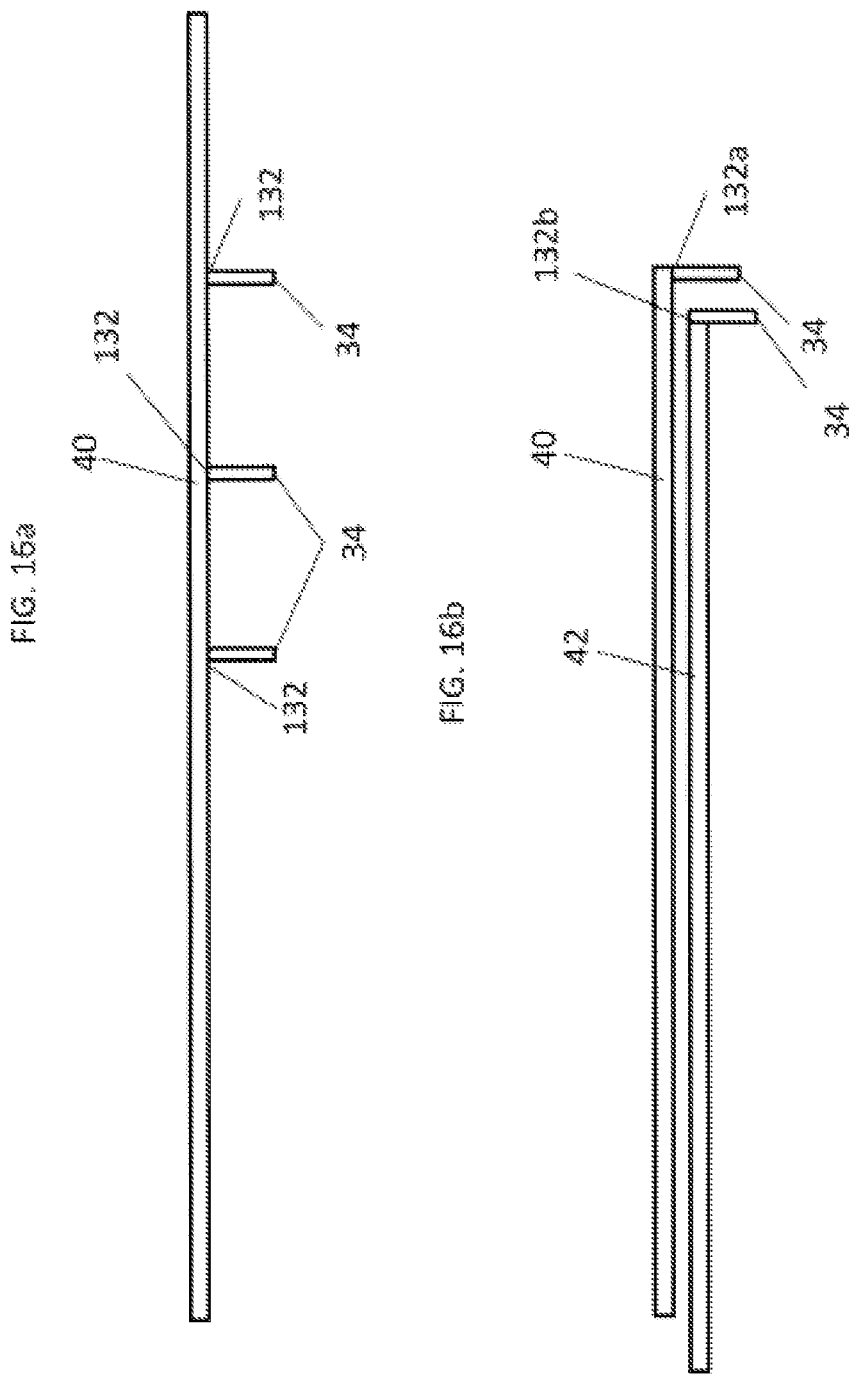
FIG. 16A is a schematic diagram of a detection system having a splice connection.
FIG. 16B is another schematic diagram of a splice connection for a detection system.

In some embodiments, such as shown in FIG. 16A, the fiber optic branches 32 are each operably connected to the fiber harness backbone 31, which may only include a single fiber optic core, via a coupling 132. In some embodiments, the coupling 132 is one of a splice connection, a fused connection or a solid state switching device. Utilizing couplings 132 allows nodes 34 to be added to the fiber harness 30 after installation of the fiber harness 30, or removal or relocation of the nodes 34 once the fiber harness 30 is installed. The couplings 132 therefore increase flexibility of the fiber harness 30 and the system 20.

In another embodiment, such as shown in FIG. 16B, a first fiber optic core 40 is operably coupled to a first node 34, while a second node 34 is operably coupled to a second fiber optic core 42. In such embodiments, the first fiber optic core 40 is utilized for transmission of light from the light source 36, while the second fiber optic core 42 receives scattered light and conveys the scatter light to the light sensitive device 38. In some embodiments, a first coupling 132a coupling the first fiber optic core 40 to the first node 34 is the same as a second coupling 132b coupling the second fiber optic core 42 to the second node 34, while in other embodiment the first coupling 132a is different from the second coupling 132b.

Figure 17:
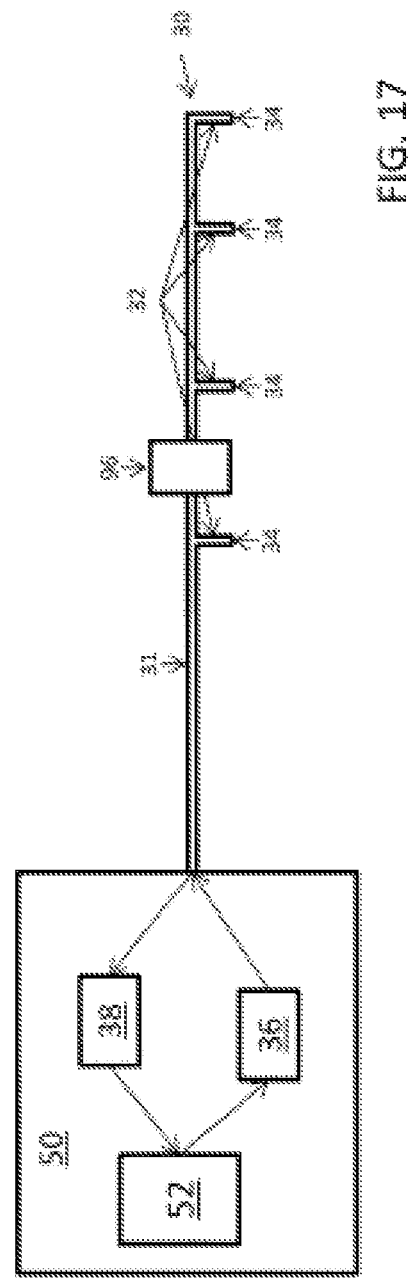
FIG. 17 is a schematic diagram of a detection system including an optical amplifier.

Further, as an alternative to or in addition to the splice connection, fused connections, one or more solid state switching devices, optical amplifiers 96 may be placed along the fiber harness 30 to amplify signals proceeding through the fiber harness 31. The optical amplifier 96 may be located, for example as shown in FIG. 17, between nodes 34, or between the light detection device 38 and the fiber harness 30. Further, in some embodiments, coupling 132 may be located at other locations along the fiber harness 30, for example, between the fiber harness 30 and the light source 36, and/or between the fiber harness 30 and the light sensitive device 38.

Figure 18:
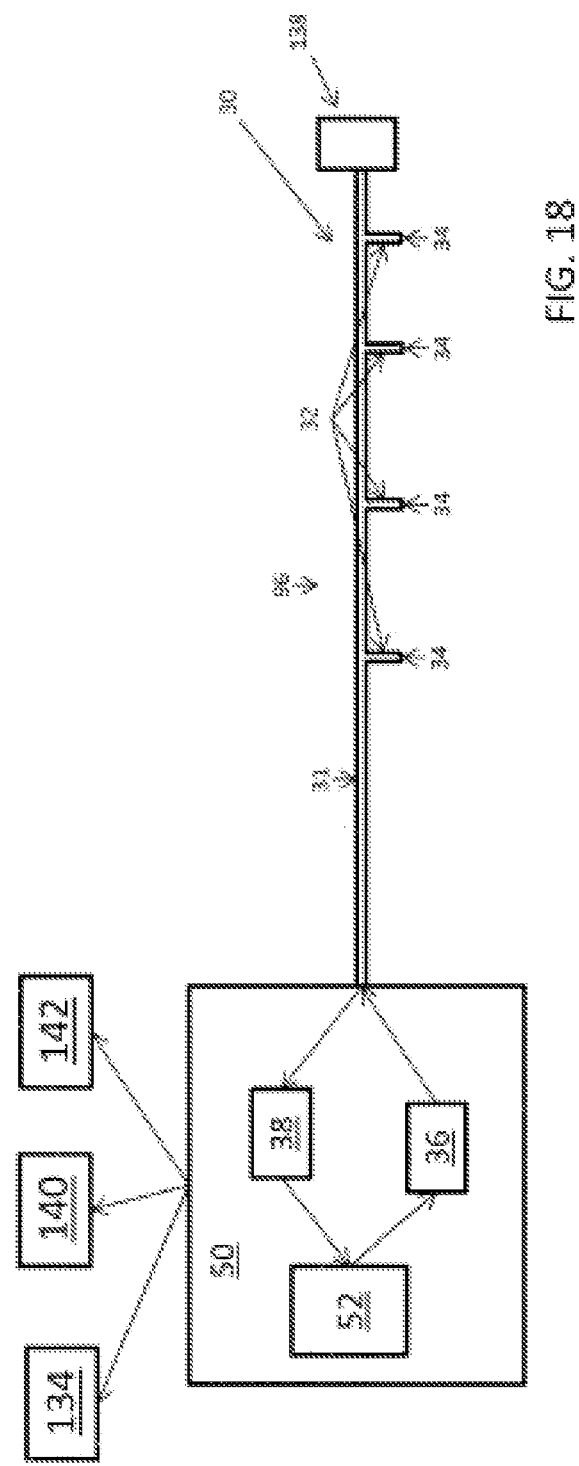
FIG. 18 is a schematic diagram of a detection system further configured for communication.

Referring now to FIG. 18, the control system 50 is configured for multiple inputs and/or multiple outputs for communication of information through the fiber optic cables 28 and the nodes 34. In some embodiments, the multiple inputs and outputs may include an internet connection 140, a building network or management system 142, and/or a fire panel 134 of the building or enclosed space. The fire panel 134 is configured for communications with, for example, a fire department, and/or is configured to transmit alarms through the building or space in the event of detection of smoke, fire or other substance by the system 20. In the embodiment shown in FIG. 18, the fiber optic cables 28 are further utilized for the communication of alarms, alerts and other information, such as system diagnostic information through the building. The control system 50 is able to both measure the condition in the predetermined area 82 and provide communication. For example, once the control system 50 determines that a condition is present based on detection signals received from one or more nodes 34, the control system 50 transmits one or more alarm signals from the fire panel 134 along fiber optic cables 28 to one or more alarm units 138 in the building or space which initiate an alarm or alert based on the received alarm signals. The control system 50 is able to do this in a fiber optic harness 30 by combining frequency and amplitude modulation of the light. In some embodiments, the alert or alarm is an audible sound or sounds, while in other embodiments the alert or alarm is a light, or a combination of light and sound. Further, the control system 50 may be configured to send and/or receive communication through the fiber optic cables 28 and the nodes 34 to communicate with one or more building infrastructure or local devices in the space via modulated light transmitted along the cables 32. In some embodiments, this communication is via Li-Fi protocol.

Figure 19:
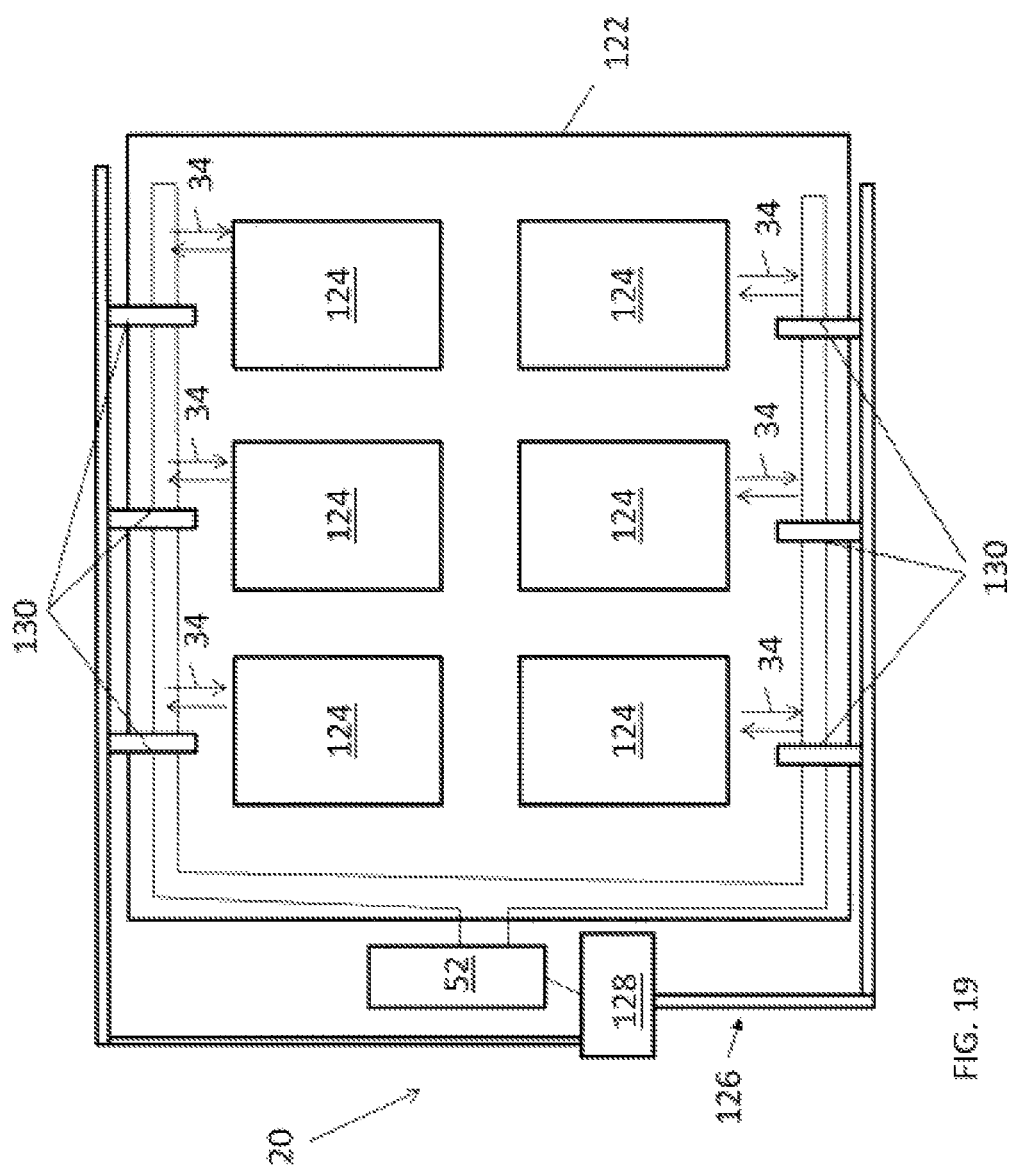
FIG. 19 is a schematic illustration of a combined detection system and suppression system.

Referring now to FIG. 19, shown is an enclosure 122, for example, a server housing, with one or more electronic components 124 located therein. A detection system 20 is installed in the enclosure 122, along with a suppression system 126. The suppression system 126 may include, for example, a suppressant supply 128 and one or more suppressant outlets 130 located at, for example, nodes 34 of the detection system 20. The detection system 20, the suppression system 126 and the one or more electronic components 124 are connected to the control unit 52 of the detection system 20. In the event of detection of fire or smoke at a node 34 of the detection system 20, the control unit 52 triggers the suppression system 126 to activate the suppressant outlet 130 at the node 34 location to provide localized suppression in the enclosure 122. Further, the control unit 52 may command powering down of electronic components 124 in the node 34 region to prevent further damage to the particular electronic components 124. Localized detection and suppression such as described herein via detection system 20 and suppression system 126, provides protection of electronic components 124 from fire and smoke, while localizing suppression to protect such components not subjected to fire and smoke from exposure to suppressant, reducing damage to those components and further reducing cost and expense of suppressant cleanup after an event.

Figure 20:
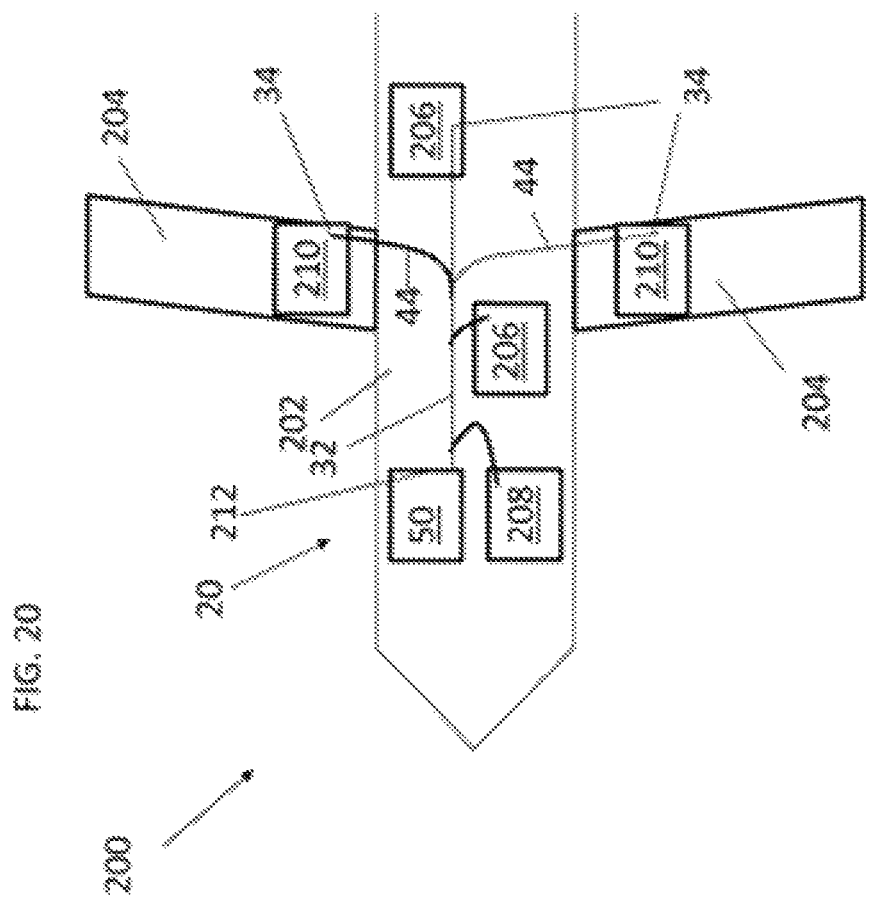
FIG. 20 is a schematic view of an aircraft.

Referring now to FIG. 20, shown is a schematic view of an aircraft 200. The aircraft 200 includes a fuselage 202 with wings 204 extending therefrom. Further, the aircraft 200 includes one or more compartments, i.e. the predetermined area, at which it is desired to provide fire, smoke and/or heat detection capabilities. These compartments may include a cargo bay 206, a lavatory 208, an avionics bay 210 or the like. One skilled in the art will readily recognize that the listed compartments are exemplary and that the present disclosure may be readily applied to other compartments, and that further the disclosure may be utilized in other vehicles or structures other than aircraft 200.

Embodiments of detection system 20 are installed in the aircraft 200 to detect fire, smoke and/or heat at the compartments 206, 208, 210. As shown in FIG. 20, a fiber harness 30 is connected to a control system 50 at a port 212 and can have one or more fiber optic cables 28 extending to the compartments 206, 208, 210. In some embodiments, different fiber optic cables 28 or fiber optic cores in the fiber harness 30 will be used for smoke/fire detection, while others are used for temperature measurements. However, the control system 50 is utilized to evaluate scattered light from the fiber harness 30 for both smoke detection and temperature/overheat detection.

A comparison of the light transmitted by the light source 36 and scattered light received at the light sensitive device 38 will indicate whether or not changes in the atmosphere adjacent to the node 34 are present. For example, the presence of smoke or other particles in the atmosphere will cause the light emitted through the node to scatter outside of the fiber. Although the detection system 20 is described as using light scattering to determine a condition or event, embodiments where light obscuration, absorption, and fluorescence is used in addition to or in place of light scattering are also within the scope of the disclosure.

In some embodiments, a first fiber optic cable 28 is utilized to monitor a compartment or area for smoke and/or fire conditions, while a second fiber optic cable 28 is utilized to monitor a compartment or area for temperature conditions. Between the port 212 and the node 34, the first fiber optic cable 28 extends into or through one or more compartments of interest for the detection system 20 to monitor or detect smoke and/or fire in the compartments. Similarly, between the port 212 and the node 34, the second fiber optic cable 28 extends into or through one or more compartments of interest for the detection system 20 to monitor or detect overheat conditions in the compartments. The second fiber optic cable can also be extended through one or more compartments in a loop.

While smoke/fire detection is done by observing the scattered light near the node 34 (not inside the fiber), the temperature can be monitored by analyzing the internal scattering in the fiber. An increase in the temperature of the ambient air surrounding the fiber optic cables 28 will cause Rayleigh and Raman scattering inside the fiber optic core(s). This internal scattering can then be correlated to a temperature of the ambient air near the core 40, 42. A location of any smoke, fire and/or overtemperature conditions is determined by analyzing the scattered light signals and time-of-flight information at the control system 50. Further, in some embodiments, the outbound light from the light source 26 may be repeated at multiple wavelengths to reduce false alarms, provide health monitoring thru strain and temperature sensing, end of life conditions or environmental health monitoring of volatile organic compounds (VOCs).

While the disclosure has been described in detail in connection with only a limited number of embodiments, it should be readily understood that the disclosure is not limited to such disclosed embodiments. Rather, the invention can be modified to incorporate any number of variations, alterations, substitutions or equivalent arrangements not heretofore described, but which are commensurate with the spirit and scope of the disclosure. Additionally, while various embodiments of the disclosure have been described, it is to be understood that aspects of the disclosure may include only some of the described embodiments. Accordingly, the disclosure is not to be seen as limited by the foregoing description, but is only limited by the scope of the appended claims.

What is claimed is:

1. A method of monitoring smoke, fire, and temperature conditions comprising:
   transmitting light from a light source and through a first fiber optic cable of a fiber harness, the fiber optic cable terminating at a node disposed to monitor a smoke or fire condition at one or more predetermined areas, the first fiber cable branching off from the fiber harness at a fiber branch portion of the first fiber cable, the fiber branch portion terminating at the node;
   transmitting light from the light source and along a second fiber optic cable of the fiber harness, the second fiber optic cable arranged to monitor a temperature condition at one or more predetermined areas;
   receiving scattered light from the first fiber optic cable and the second fiber optic cable at a control system via a light sensitive device; and
   analyzing the scattered light to determine at least one of the presence and magnitude of smoke, fire and/or a temperature condition along the fiber harness or at the node;
   wherein the temperature condition at one or more fiber portions of the second fiber optic cable is determined by analyzing the scattered light that has been internally scattered in the second fiber optic cable at the one or more fiber portions and received at the light sensitive device.

2. The method according to claim 1, wherein the light source is selectively operable to transmit the light signal.

3. The method according to claim 1, further comprising selectably changing a wavelength of the transmitted light.

4. The method according to claim 1, wherein the light sensitive device is associated with the node, the light sensitive device configured to receive the scattered light signal.

5. The method according to claim 1, further comprising converting the scattered light signal into corresponding electrical signals for evaluation by a control unit.

6. A system for monitoring smoke, fire and/or temperature conditions within an aircraft structure comprising:
   a fiber harness comprising a first fiber optic cable terminating at a node disposed to monitor a smoke or fire condition at one or more predetermined areas and a second fiber optic cable arranged to monitor a temperature condition at one or more predetermined areas, the first fiber cable branching off from the fiber harness at a fiber branch portion of the first fiber cable, the fiber branch portion terminating at the node; and
   a control system operably connected to the fiber harness, the control system comprising:
      one or more light sensitive devices configured to receive light from the first fiber optic cable and the second fiber optic cable; and
      a control unit configured to:
         analyze light received at the one or more light sensitive devices from the first fiber optic cable to determine one or more fire or smoke conditions at one or more predetermined areas; and
         analyze light received at the one or more light sensitive devices from the second fiber optic cable to determine the temperature conditions at one or more predetermined areas;
      wherein the temperature condition at the one or more predetermined areas is determined by analyzing the scattered light that has been internally scattered in the second fiber optic cable at one or more fiber portions of the second fiber optic cable disposed at the one or more predetermined areas and received at the light sensitive device.

7. The system according to claim 6, wherein measuring the temperature further comprises determining an overheat condition.

8. The system according to claim 6, wherein the one or more light sensitive devices comprises a first light sensitive device configured to receive light from the first fiber optic cable and a second light sensitive device configured to receive light from the second fiber optic cable.

9. The system according to claim 6, wherein the control system includes a light source for transmitting the light signal along the first fiber optic cable and the second fiber optic cable.

10. The system according to claim 9, wherein the control unit is operably coupled to the light source to selectively control emission of light from the light source.

11. The system according to claim 6, wherein the light sensitive device is a photodiode.

12. The system according to claim 6, wherein the light sensitive device converts the scattered light signal received at the control system into an electrical signal receivable by the control unit.

13. The system according to claim 6, wherein the first fiber optic cable defines a plurality of nodes arranged within the aircraft structure.

14. The system according to claim 6, wherein the aircraft structure is one or more of a cargo compartment, an avionics bay or other enclosed portion of the aircraft.

15. A method of monitoring a temperature condition comprising:

transmitting light along a fiber optic cable, the fiber optic cable arranged to monitor a temperature condition at one or more predetermined areas, the fiber optic cable including a plurality of branches, each branch of the plurality of branches terminating at a node, the light transmitted along the fiber optic cable and through the node;

receiving scattered light from the fiber optic cable;

communicating the scattered light to a light sensitive device; and determining, via the control system, whether the scattered light indicates a presence of an undesirable temperature condition along the fiber harness and/or at the node;

wherein the temperature condition at one or more fiber portions of the fiber optic cable is determined by analyzing the scattered light that has been internally scattered in the fiber optic cable at the one or more fiber portions and received at the light sensitive device.

16. The method according to claim 15, wherein the light source is selectively operable to transmit the light signal.

17. The method according to claim 15, further comprising selectably changing a wavelength of the transmitted light.

* * * * *